(12) United States Patent  (10) Patent No.: US 9,346,785 B2
Lukin  (45) Date of Patent: May 24, 2016

(54) PROCESS FOR MAKING HCV PROTEASE INHIBITORS

(71) Applicant: AbbVie Inc., Abbott Park, IL (US)

(72) Inventor: Kirill A. Lukin, Vernon Hills, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/739,174

(22) Filed: Jan. 11, 2013

(65) Prior Publication Data
US 2013/0178630 A1 Jul. 11, 2013

Related U.S. Application Data

(60) Provisional application No. 61/585,280, filed on Jan. 11, 2012.

(51) Int. Cl.
C07D 231/56 (2006.01)
C07D 207/00 (2006.01)
C07D 295/00 (2006.01)
C07D 221/12 (2006.01)
C07D 401/14 (2006.01)
(Continued)

(52) U.S. Cl.
CPC ............ *C07D 401/14* (2013.01); *C07D 231/56* (2013.01); *C07D 401/12* (2013.01); *C07K 5/06165* (2013.01); *C07K 5/0808* (2013.01); Y02P 20/582 (2015.11)

(58) Field of Classification Search
None
See application file for complete search history.

(56) References Cited

FOREIGN PATENT DOCUMENTS

WO    WO-2006/138187 A1    12/2006
WO    WO-2007/014919 A1    2/2007
(Continued)

OTHER PUBLICATIONS

Conrow, R. E. et al., "Two-step N-acylindazole to N-alkylindazole reduction. Further synthetic studies on the serotonergic agonist AL-34662", *Tetrahedron Letters*, 49:2348-2350 (Elsevier Ltd., 2008).

(Continued)

*Primary Examiner* — Rita Desai
*Assistant Examiner* — Ben S Michelson
(74) *Attorney, Agent, or Firm* — Dana M. Gordon; Foley Hoag LLP

(57) ABSTRACT

Efficient processes for making HCV protease inhibitors are described. In one embodiment, the process uses novel idazolide derivatives of vinyl-ACCA. In another embodiment, the process comprises reacting

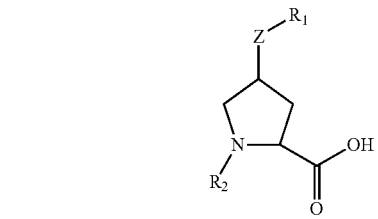

with

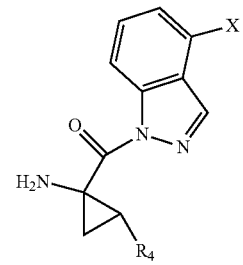

to form

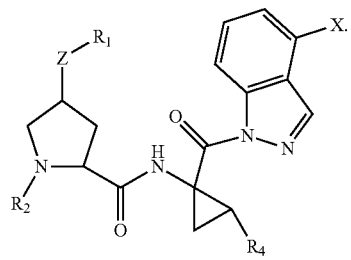

In still another embodiment, the process comprises coupling

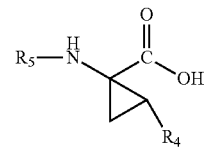

with

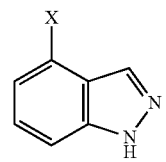

to form

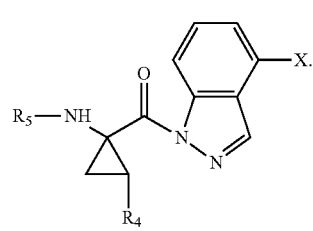

6 Claims, No Drawings

(51) Int. Cl.
*C07K 5/083* (2006.01)
*C07K 5/078* (2006.01)
*C07D 401/12* (2006.01)

(56) References Cited

FOREIGN PATENT DOCUMENTS

| WO | WO 2007/014919 A1 | * | 2/2007 |
| WO | WO-2008/016993 A1 | | 2/2008 |
| WO | WO-2011/034518 A1 | | 3/2011 |

OTHER PUBLICATIONS

International Preliminary Report on Patentability from related PCT application PCT/US2013/021118 dated Jul. 15, 2014.
International Search Report from related PCT application PCT/US2013/021118 dated Mar. 5, 2013.

* cited by examiner

PROCESS FOR MAKING HCV PROTEASE INHIBITORS

CROSS-REFERENCES TO RELATED APPLICATIONS

This application claims priority to U.S. Provisional Application Ser. No. 61/585,280 filed Jan. 11, 2012, which is incorporated by reference in its entirety.

FIELD

The present invention relates to processes for making Hepatitis C virus ("HCV") protease inhibitors.

BACKGROUND

HCV is the principal cause of non-A, non-B hepatitis and is an increasingly severe public health problem both in the developed and developing world. It is estimated that the virus infects over 200 million people worldwide, surpassing the number of individuals infected with the human immunodeficiency virus (HIV) by nearly five fold. HCV infected patients, due to the high percentage of individuals inflicted with chronic infections, are at an elevated risk of developing cirrhosis of the liver, subsequent hepatocellular carcinoma and terminal liver disease. HCV is the most prevalent cause of hepatocellular cancer and cause of patients requiring liver transplantations in the western world.

DETAILED DESCRIPTION

The present invention features processes for making HCV protease inhibitors. The HCV protease mediates the cleavage of the HCV polyprotein to release the functional proteins that are essential for viral propagation. The inhibition of the HCV protease activity is expected to block HCV replication in infected host cells. Numerous HCV protease inhibitors have been identified. Non-limiting examples of HCV protease inhibitors are described in U.S. Patent Application Pub. Nos. 20040106559, 20040180815, 20040266668, 2004038872, 20050090432, 20050267018, 20070054842, 20070281885, 2007299078, 20080032936, 20080125444, 20080279821, 20090111757, 20090148407, 20090202480, 20090269305, 20090285773, 20090285774, 20100081700, 20100144608, 2010018355, 20100183551, 20100221217, 20100260710, 20100286185 and 20110135604, and U.S. Pat. Nos. 6,608,027, 6,767,991, 7,091,184, 7,119,072, 7,544,798, 7,642,235 and 7,829,665, as well as WO2007014919, WO2007014926, WO2008046860, WO2008095058, WO2009139792, WO2010122087, and WO2011034518. Most of these protease inhibitors contain

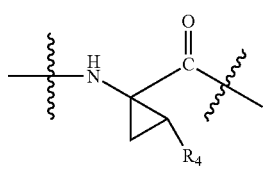

or an equivalent moiety, where $R_4$ is optionally substituted $C_1$-$C_6$alkyl, optionally substituted $C_2$-$C_6$alkenyl, or optionally substituted $C_2$-$C_6$alkynyl, and preferably $R_4$ is vinyl.

The present invention features novel and efficient processes for incorporating

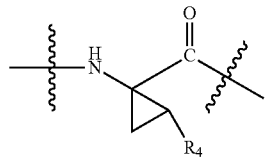

or an equivalent moiety into HCV protease inhibitors. These processes are often high yielding and readily scalable. In one aspect, the processes comprise reacting a compound of Formula I with a compound of Formula II to form a compound of Formula III,

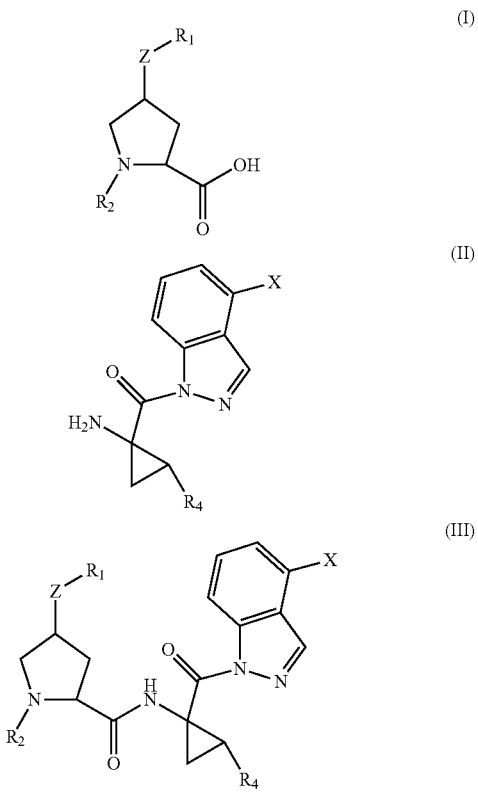

wherein Z is O, S, SO, SO2, N($R_N$), OC(O), C(O)O, N($R_N$)C(O), or C(O)N($R_N$), wherein $R_N$ is H or optionally substituted $C_1$-$C_6$alkyl; $R_1$ is optionally substituted carbocycle or optionally substituted heterocycle; $R_2$ is H or an amino protecting group; $R_4$ is optionally substituted $C_1$-$C_6$alkyl, optionally substituted $C_2$-$C_6$alkenyl, or optionally substituted $C_2$-$C_6$alkynyl; and X is H or halogen. In one embodiment, the process further comprises reacting the compound of Formula III with $R_3$—OH to form

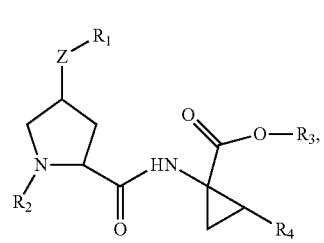

wherein R₃ is optionally substituted $C_1$-$C_6$ alkyl or a carboxyl protecting group.

Suitable amino protecting groups include, but are not limited to, carbobenzyloxy (Cbz) group, p-methoxybenzyl carbonyl (Moz or MeOZ) group, tert-butyloxycarbonyl (BOC) group, 9-Fluorenylmethyloxycarbonyl (FMOC) group, acetyl (Ac) group, benzoyl (Bz) group, benzyl (Bn) group, carbamate group, p-Methoxybenzyl (PMB), 3,4-Dimethoxybenzyl (DMPM), p-methoxyphenyl (PMP) group, tosyl (Ts) group, or sulfonamides (e.g., Nosyl & Nps) groups. Preferably, $R_2$ is tert-butyloxycarbonyl.

Suitable carboxyl protecting groups include, but are not limited to, methyl esters, benzyl esters, tert-butyl esters, silyl esters, orthoesters, or oxazoline. Preferably, $R_3$ is a —$CH_2CH_3$.

In one embodiment, Z is O; $R_1$ is phenanthridine; $R_2$ is an amino protecting group; $R_4$ is -vinyl; X is H or Cl.

In another embodiment, the compound of Formula I is

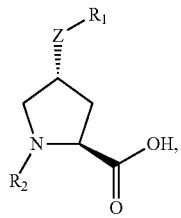

the compound of Formula II is

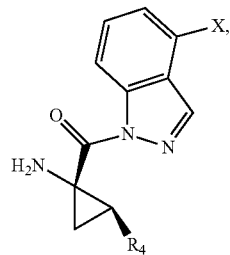

and the compound of Formula III is

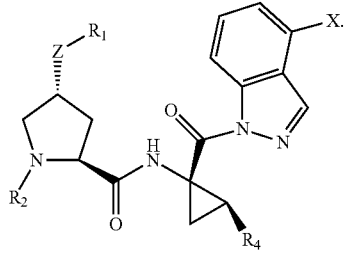

Preferably, Z is O; $R_1$ is phenanthridine; $R_2$ is an amino protecting group; $R_4$ is vinyl; X is H or Cl. Also preferably, $R_2$ is tert-butyloxycarbonyl. The process may further comprise reacting the compound of Formula III with $R_3$—OH to form

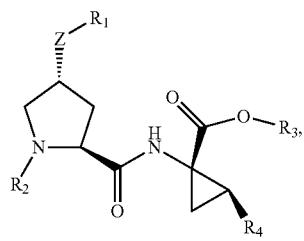

wherein $R_3$ is optionally substituted $C_1$-$C_6$ alkyl or a carboxyl protecting group. Preferably, $R_3$ is a —$CH_2CH_3$.

HCV protease inhibitors that can be prepared according to the present invention include, but are not limited to,

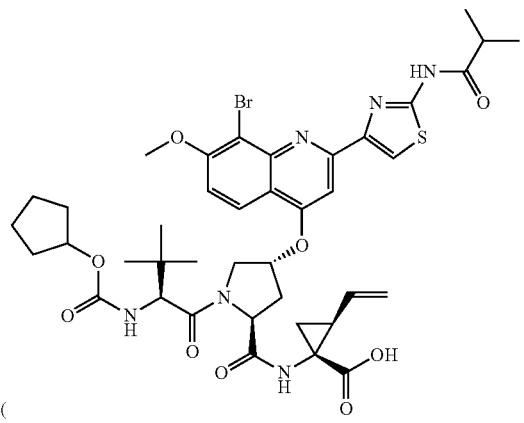

BI-201335

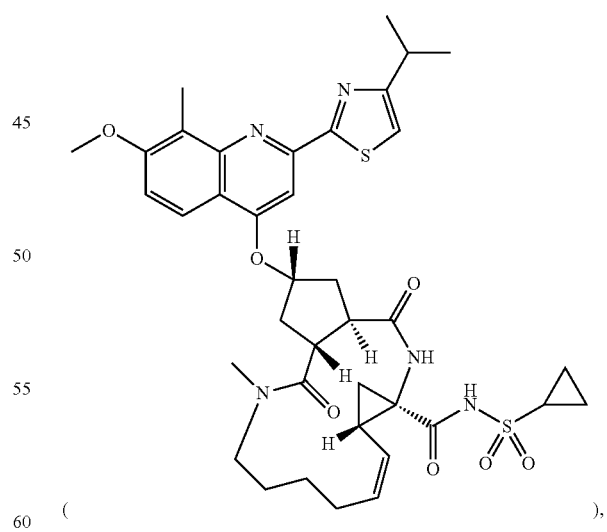

TMC-435350 vaniprevir ((1R,21S,24S)-21-tert-butyl-N-((1R,2R)-1-{[(cyclopropylsulfonyl)amino]carbonyl}-2-ethylcyclopropyl)-16,16-dimethyl-3,19,22-trioxo-2,18-dioxa-4,20,23-triazatetracyclo[21.2.1.1⁴,⁷.0⁶,¹¹]-heptacosa-6,8,10-trene-24-carboxamide), MK-5172
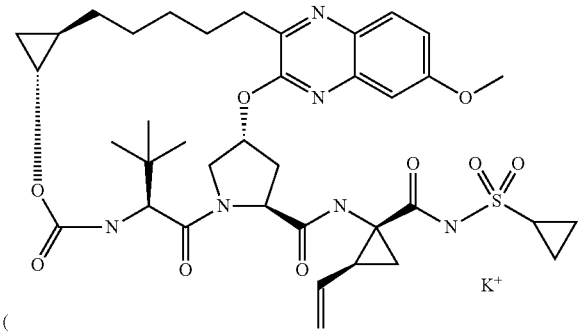
BMS-650032
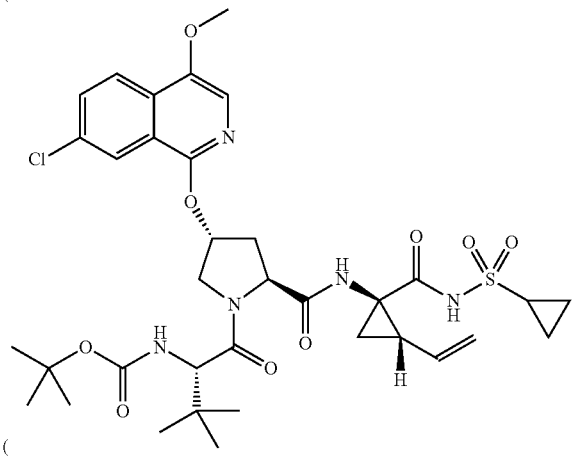
danoprevir
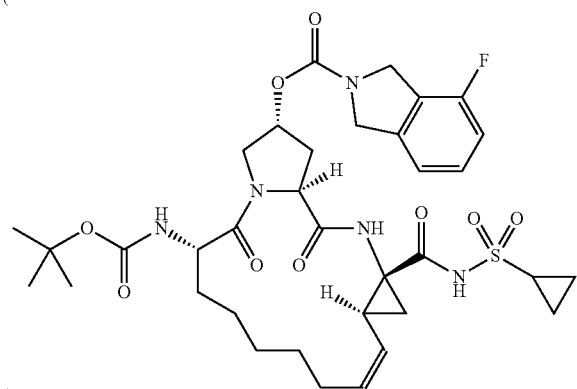
GS-9451
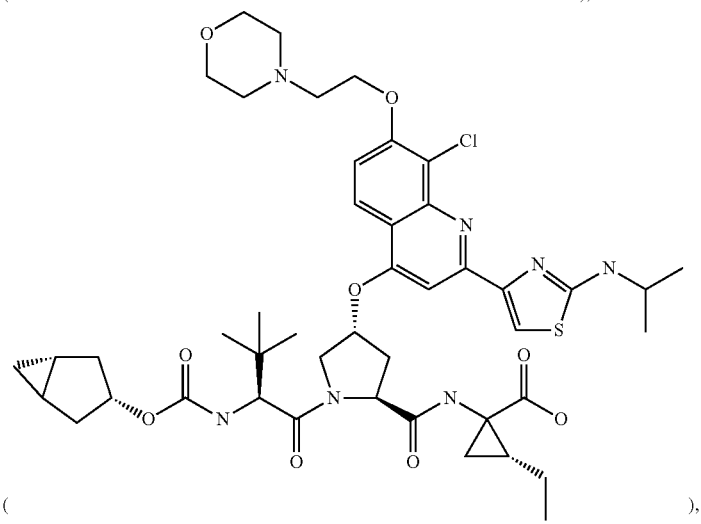

and Compound I ((2R,6S,13aS,14aR,16aS,Z)—N-(cyclopropylsulfonyl)-6-(5-methylpyrazine-2-carboxamido)-5,16-dioxo-2-(phenanthridin-6-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide, described in U.S. Patent Application Publication No. 2010/0144608).

In another aspect, the present invention features processes for making

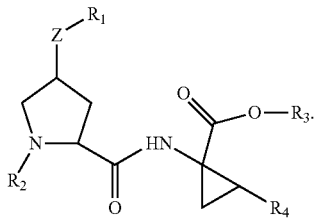

The processes comprise reacting

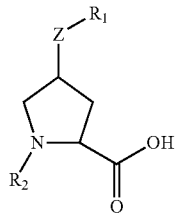

with

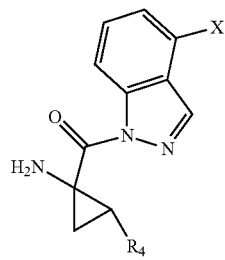

to form

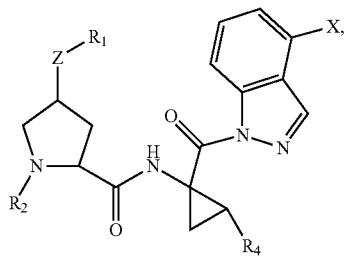

wherein Z is O, S, SO, SO2, N(R$_N$), OC(O), C(O)O, N(R$_N$)C(O), or C(O)N(R$_N$), wherein R$_N$ is H or optionally substituted C$_1$-C$_6$alkyl; R$_1$ is optionally substituted carbocycle or optionally substituted heterocycle; R$_2$ is H or an amino protecting group; R$_4$ is optionally substituted C$_1$-C$_6$alkyl, optionally substituted C$_2$-C$_6$alkenyl, or optionally substituted C$_2$-C$_6$alkynyl; X is H or halogen; and R$_3$ is H, optionally substituted C$_1$-C$_6$alkyl or a carboxyl protecting group. Preferably, Z is O; R$_1$ is phenanthridine; R$_2$ is an amino protecting group; R$_4$ is vinyl; X is H or Cl. Also preferably, R$_2$ is tert-butyloxycarbonyl. Also preferably, R$_3$ is a —CH$_2$CH$_3$.

In yet another aspect, the present invention features processes for making

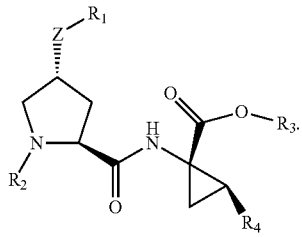

The processes comprise reacting

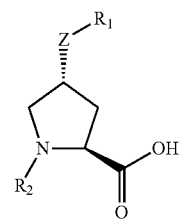

with

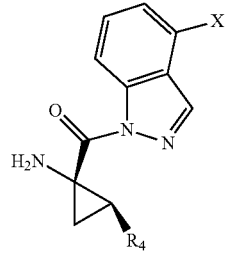

to form

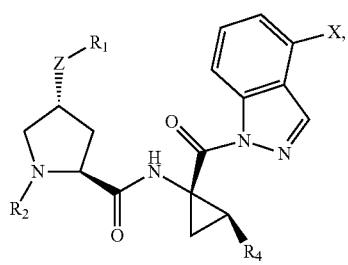

wherein Z is O, S, SO, SO2, N(R$_N$), OC(O), C(O)O, N(R$_N$)C(O), or C(O)N(R$_N$), wherein R$_N$ is H or optionally substituted C$_1$-C$_6$alkyl;

R$_1$ is optionally substituted carbocycle or optionally substituted heterocycle; R$_2$ is H or an amino protecting group; R$_4$ is optionally substituted C$_1$-C$_6$alkyl, optionally substituted C$_2$-C$_6$alkenyl, or optionally substituted C$_2$-C$_6$alkynyl; X is H or halogen; and $R_3$ is H, optionally substituted C1-C6alkyl or a carboxyl protecting group. The process may also comprise reacting

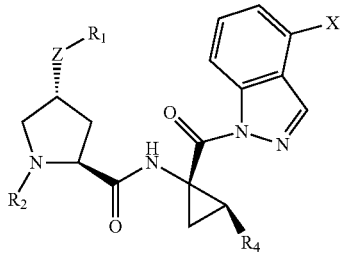

with $R_3$—OH to form

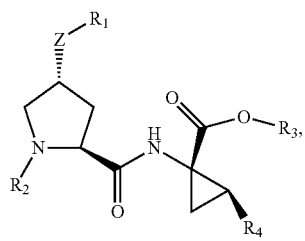

wherein $R_3$ is optionally substituted $C_1$-$C_6$alkyl or a carboxyl protecting group. Preferably, Z is O; $R_1$ is phenanthridine; $R_2$ is an amino protecting group; $R_4$ is vinyl; X is H or Cl. Also preferably, $R_2$ is tert-butyloxycarbonyl. Also preferably, $R_3$ is a —$CH_2CH_3$.

The present invention also features processes for making

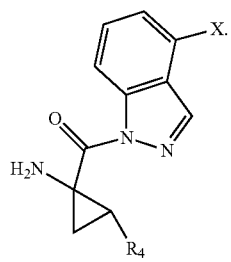

The processes comprise reacting

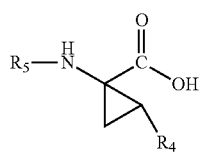

with

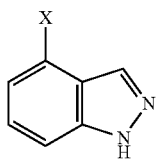

to form

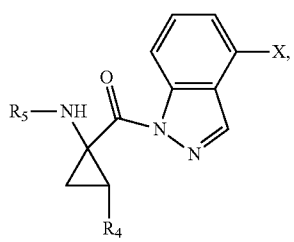

wherein $R_4$ is optionally substituted $C_1$-$C_6$alkyl, optionally substituted $C_2$-$C_6$alkenyl, or optionally substituted $C_2$-$C_6$alkynyl; X is H or halogen; and $R_5$ is H or an amino protecting group. When $R_5$ is an amino protecting group, the processes may further comprise deprotecting

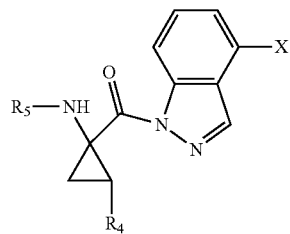

to form

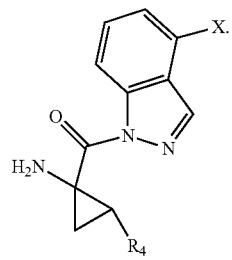

Preferably, $R_4$ is vinyl. Also preferably, $R_5$ is tert-butyloxycarbonyl. In one embodiment, the process comprises reacting

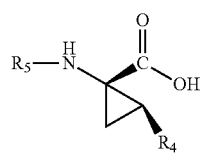

with

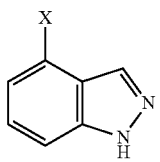

to form

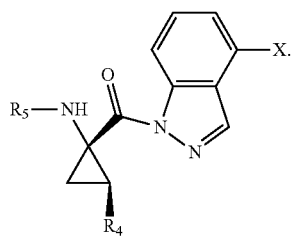

As used herein,

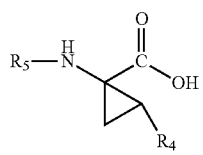

(including its various stereoisomers) can be prepared according to the processes described in EP2345633 A1 (Kaneka Corp.)

In addition, the present invention features compounds having the formula

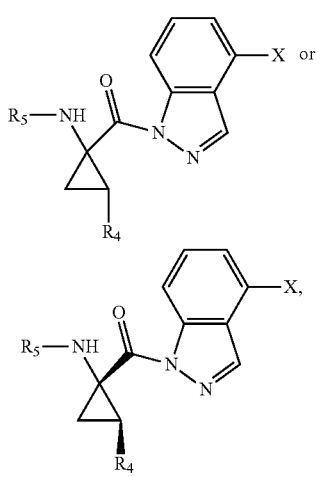

wherein $R_4$ is optionally substituted $C_1$-$C_6$alkyl, optionally substituted $C_2$-$C_6$alkenyl, or optionally substituted $C_2$-$C_6$alkynyl; X is H or halogen; and $R_5$ is H or an amino protecting group. Preferably, $R_5$ is H. Preferably, $R_4$ is vinyl.

The compounds employed in the invention may comprise asymmetrically substituted carbon atoms known as chiral centers. These compounds may exist, without limitation, as single stereoisomers (e.g., single enantiomers or single diastereomer), mixtures of stereoisomers (e.g. a mixture of enantiomers or diastereomers), or racemic mixtures. Compounds identified herein as single stereoisomers are meant to describe compounds that are present in a form that is substantially free from other stereoisomers (e.g., substantially free from other enantiomers or diastereomers). By "substantially free," it means that at least 80% of the compound in a composition is the described stereoisomer; preferably, at least 90% of the compound in a composition is the described stereoisomer; and more preferably, at least 95%, 96%, 97%, 98% or 99% of the compound in a composition is the described stereoisomer. Where the stereochemistry of a chiral carbon is not specified in the chemical structure of a compound, the chemical structure is intended to encompass compounds containing either stereoisomer of the chiral center.

Individual stereoisomers of the compounds employed in this invention can be prepared using a variety of methods known in the art. These methods include, but are not limited to, stereospecific synthesis, chromatographic separation of diastereomers, chromatographic resolution of enantiomers, conversion of enantiomers in an enantiomeric mixture to diastereomers followed by chromatographically separation of the diastereomers and regeneration of the individual enantiomers, and enzymatic resolution.

Stereospecific synthesis typically involves the use of appropriate optically pure (enantiomerically pure) or substantial optically pure materials and synthetic reactions that do not cause racemization or inversion of stereochemistry at the chiral centers. Mixtures of stereoisomers of compounds, including racemic mixtures, resulting from a synthetic reaction may be separated, for example, by chromatographic techniques as appreciated by those of ordinary skill in the art. Chromatographic resolution of enantiomers can be accomplished by using chiral chromatography resins, many of which are commercially available. In a non-limiting example, racemate is placed in solution and loaded onto the column containing a chiral stationary phase. Enantiomers can then be separated by HPLC.

Resolution of enantiomers can also be accomplished by converting enantiomers in a mixture to diastereomers by reaction with chiral auxiliaries. The resulting diastereomers can be separated by column chromatography or crystallization/re-crystallization. This technique is useful when the compounds to be separated contain a carboxyl, amino or hydroxyl group that will form a salt or covalent bond with the chiral auxiliary. Non-limiting examples of suitable chiral auxiliaries include chirally pure amino acids, organic carboxylic acids or organosulfonic acids. Once the diastereomers are separated by chromatography, the individual enantiomers can be regenerated. Frequently, the chiral auxiliary can be recovered and used again.

Enzymes, such as esterases, phosphatases or lipases, can be useful for the resolution of derivatives of enantiomers in an enantiomeric mixture. For example, an ester derivative of a carboxyl group in the compounds to be separated can be treated with an enzyme which selectively hydrolyzes only one of the enantiomers in the mixture. The resulting enantiomerically pure acid can then be separated from the unhydrolyzed ester.

Alternatively, salts of enantiomers in a mixture can be prepared using any suitable method known in the art, including treatment of the carboxylic acid with a suitable optically pure base such as alkaloids or phenethylamine, followed by precipitation or crystallization/re-crystallization of the enantiomerically pure salts. Methods suitable for the resolution/separation of a mixture of stereoisomers, including racemic mixtures, can be found in ENANTIOMERS, RACEMATES, AND RESOLUTIONS (Jacques et al., 1981, John Wiley and Sons, New York, N.Y.).

The number of carbon atoms in a hydrocarbyl moiety can be indicated by the prefix "$C_x$-$C_y$," where x is the minimum and y is the maximum number of carbon atoms in the moiety. Thus, for example, "$C_1$-$C_6$alkyl" refers to an alkyl substituent containing from 1 to 6 carbon atoms.

When a chemical formula is used to describe a moiety, the dash(es) indicates the portion of the moiety that has the free valence(s).

If a moiety is described as being "optionally substituted", the moiety may be either substituted or unsubstituted. If a moiety is described as being optionally substituted with up to a particular number of non-hydrogen radicals, that moiety may be either unsubstituted, or substituted by up to that particular number of non-hydrogen radicals or by up to the maximum number of substitutable positions on the moiety, whichever is less. Thus, for example, if a moiety is described as a heterocycle optionally substituted with up to three non-hydrogen radicals, then any heterocycle with less than three substitutable positions will be optionally substituted by up to only as many non-hydrogen radicals as the heterocycle has substitutable positions.

Where a moiety is substituted with oxo or thioxo, it means that the moiety contains a carbon atom covalently bonded to at least two hydrogens (e.g., $CH_2$), and the two hydrogen radicals are substituted with oxo or thioxo to form C=O or C=S, respectively.

The term "alkenyl" means a straight or branched hydrocarbyl chain containing one or more double bonds. Each carbon-carbon double bond may have either cis or trans geometry within the alkenyl moiety, relative to groups substituted on the double bond carbons. Non-limiting examples of alkenyl groups include ethenyl (vinyl), 2-propenyl, 3-propenyl, 1,4-pentadienyl, 1,4-butadienyl, 1-butenyl, 2-butenyl, and 3-butenyl.

The term "alkyl" means a straight or branched saturated hydrocarbyl chain. Non-limiting examples of alkyl groups include methyl, ethyl, n-propyl, isopropyl, n-butyl, isobutyl, sec-butyl, t-butyl, pentyl, iso-amyl, and hexyl.

The term "alkynyl" means a straight or branched hydrocarbyl chain containing one or more triple bonds. Non-limiting examples of alkynyl include ethynyl, 1-propynyl, 2-propynyl, 3-propynyl, decynyl, 1-butynyl, 2-butynyl, and 3-butynyl.

The term "carbocycle" refers to a saturated (e.g., "cycloalkyl"), partially saturated (e.g., "cycloalkenyl" or "cycloalkynyl") or completely unsaturated (e.g., "aryl") ring system containing zero heteroatom ring atom. "Ring atoms" or "ring members" are the atoms bound together to form the ring or rings. A carbocycle may be, without limitation, a single ring, two fused rings, or bridged or spiro rings. A substituted carbocycle may have either cis or trans geometry. Representative examples of carbocycle include, but are not limited to, cyclopropyl, cyclobutyl, cyclopentyl, cyclohexyl, cycloheptyl, cyclooctyl, cyclopentenyl, cyclopentadienyl, cyclohexadienyl, adamantyl, decahydro-naphthalenyl, octahydro-indenyl, cyclohexenyl, phenyl, naphthyl, indanyl, 1,2,3,4-tetrahydro-naphthyl, indenyl, isoindenyl, decalinyl, and norpinanyl. A carbocycle group can be attached to the parent molecular moiety through any substitutable carbon ring atom.

The term "heterocycle" refers to a saturated (e.g., "heterocycloalkyl"), partially unsaturated (e.g., "heterocycloalkenyl" or "heterocycloalkynyl") or completely unsaturated (e.g., "heteroaryl") ring system where at least one of the ring atoms is a heteroatom (i.e., nitrogen, oxygen or sulfur), with the remaining ring atoms being independently selected from the group consisting of carbon, nitrogen, oxygen and sulfur. A heterocycle may be, without limitation, a single ring, two fused rings, or bridged or spiro rings. A heterocycle group can be linked to the parent molecular moiety via any substitutable carbon or nitrogen atom(s) in the group.

A heterocycle may be, without limitation, a monocycle which contains a single ring. Non-limiting examples of monocycles include furanyl, dihydrofuranyl, tetrahydrofuranyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazolyl (including 1,2,3-oxadiazolyl, 1,2,4-oxadiazolyl (also known as "azoximyl"), 1,2,5-oxadiazolyl (also known as "furazanyl"), and 1,3,4-oxadiazolyl), oxatriazolyl (including 1,2,3,4-oxatriazolyl and 1,2,3,5-oxatriazolyl), dioxazolyl (including 1,2,3-dioxazolyl, 1,2,4-dioxazolyl, 1,3,2-dioxazolyl, and 1,3,4-dioxazolyl), oxathiolanyl, pyranyl (including 1,2-pyranyl and 1,4-pyranyl), dihydropyranyl, pyridinyl, piperidinyl, diazinyl (including pyridazinyl (also known as "1,2-diazinyl"), pyrimidinyl (also known as "1,3-diazinyl"), and pyrazinyl (also known as "1,4-diazinyl")), piperazinyl, triazinyl (including s-triazinyl (also known as "1,3,5-triazinyl"), astriazinyl (also known 1,2,4-triazinyl), and v-triazinyl (also known as "1,2,3-triazinyl"), oxazinyl (including 1,2,3-oxazinyl, 1,3,2-oxazinyl, 1,3,6-oxazinyl (also known as "pentoxazolyl"), 1,2,6-oxazinyl, and 1,4-oxazinyl), isoxazinyl (including o-isoxazinyl and p-isoxazinyl), oxazolidinyl, isoxazolidinyl, oxathiazinyl (including 1,2,5-oxathiazinyl or 1,2,6-oxathiazinyl), oxadiazinyl (including 1,4,2-oxadiazinyl and 1,3,5,2-oxadiazinyl), morpholinyl, azepinyl, oxepinyl, thiepinyl, thiomorpholinyl, and diazepinyl.

A heterocycle may also be, without limitation, a bicycle containing two fused rings, such as, for example, naphthyridinyl (including [1,8]naphthyridinyl, and [1,6]naphthyridinyl), thiazolpyrimidinyl, thienopyrimidinyl, pyrimidopyrimidinyl, pyridopyrimidinyl, pyrazolopyrimidinyl, indolizinyl, pyrindinyl, pyranopyrrolyl, 4H-quinolizinyl, purinyl, pyridopyridinyl (including pyrido[3,4-b]-pyridinyl, pyrido[3,2-b]-pyridinyl, and pyrido[4,3-b]-pyridinyl), pyridopyrimidine, and pteridinyl. Other non-limiting examples of fused-ring heterocycles include benzo-fused heterocyclyls, such as indolyl, isoindolyl, indoleninyl (also known as "pseudoindolyl"), isoindazolyl (also known as "benzpyrazolyl" or indazolyl), benzazinyl (including quinolinyl (also known as "1-benzazinyl") and isoquinolinyl (also known as "2-benzazinyl")), benzimidazolyl, phthalazinyl, quinoxalinyl, benzodiazinyl (including cinnolinyl (also known as "1,2-benzodiazinyl") and quinazolinyl (also known as "1,3-benzodiazinyl")), benzopyranyl (including "chromenyl" and "isochromenyl"), benzothiopyranyl (also known as "thiochromenyl"), benzoxazolyl, indoxazinyl (also known as "benzisoxazolyl"), anthranilyl, benzodioxolyl, benzodioxanyl, benzoxadiazolyl, benzofuranyl (also known as "coumaronyl"), isobenzofuranyl, benzothienyl (also known as "benzothiophenyl", "thionaphthenyl", and "benzothiofuranyl"), isobenzothienyl (also known as "isobenzothiophenyl", "isothionaphthenyl", and "isobenzothiofuranyl"), benzothiazolyl, 4,5,6,7-tetrahydrobenzo[d]thiazolyl, benzothiadiazolyl, benzimidazolyl, benzotriazolyl, benzoxazinyl (including 1,3,2-benzoxazinyl, 1,4,2-benzoxazinyl, 2,3,1- benzoxazinyl, and 3,1,4-benzoxazinyl), benzisoxazinyl (including 1,2-benzisoxazinyl and 1,4-benzisoxazinyl), and tetrahydroisoquinolinyl.

A heterocycle may also be, without limitation, a spiro ring system, such as, for example, 1,4-dioxa-8-azaspiro[4.5]decanyl.

A heterocycle may comprise one or more sulfur atoms as ring members; and in some cases, the sulfur atom(s) is oxidized to SO or $SO_2$. The nitrogen heteroatom(s) in a heterocycle may or may not be quaternized, and may or may not be oxidized to N-oxide. In addition, the nitrogen heteroatom(s) may or may not be N-protected.

Unless specified, the term "substituted" refers to substitution by independent replacement of one, two, or three or more of the hydrogen atoms with suitable substituents. Non-limiting examples of substituents include —F, —Cl, —Br, —I, hydroxy, protected hydroxy, —$NO_2$, —$N_3$, —CN, —$NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_8$-alkenyl, —$OCO_2$—$C_2$-$C_8$-alkynyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_8$-alkenyl, —$NHCO_2$—$C_2$-$C_8$-alkynynl, —$NHCO_2$—$C_3$-$C_{12}$-cycloalkyl, —$NHCO_2$-aryl, —$NHCO_2$-heteroaryl, —$NHCO_2$-heterocycloalkyl, —$NHC(O)NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, $NHC(S)NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —$NHC(NH)NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —$SO_2NH_2$, —$SO_2NH$—$C_1$-$C_{12}$-alkyl, —$SO_2NH$—$C_2$-$C_8$-alkenyl, —$SO_2NH$—$C_2$-$C_8$-alkynyl, —$SO_2NH$—$C_3$-$C_{12}$-cycloalkyl, —$SO_2NH$-aryl, —$SO_2NH$-heteroaryl, —$SO_2NH$-heterocycloalkyl, —$NHSO_2$—$C_1$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, -heteroaryl, —S-heterocycloalkyl, or methylthiomethyl.

The term "amino protecting group" refers to those groups capable of protecting an amino group against undesirable reactions. Commonly used amino protecting groups (also known as N-protecting groups) are described in Greene and Wuts, PROTECTING GROUPS IN CHEMICAL SYNTHESIS ($3^{rd}$ ed., John Wiley & Sons, NY (1999). Non-limiting examples of N-protecting groups include acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, benzoyl, 4-chlorobenzoyl, 4-bromobenzoyl, or 4-nitrobenzoyl; sulfonyl groups such as benzenesulfonyl or p-toluenesulfonyl; sulfenyl groups such as phenylsulfenyl (phenyl-S—) or triphenylmethylsulfenyl (trityl-S—); sulfinyl groups such as p-methylphenylsulfinyl (p-methylphenyl-S(O)—) or t-butylsulfinyl (t-Bu-S(O)—); carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloro-ethoxy-carbonyl, phenoxycarbonyl, 4-nitro-phenoxycarbonyl, cyclopentyloxycarbonyl, adamantyloxycarbonyl, cyclohexyloxycarbonyl, or phenylthiocarbonyl; alkyl groups such as benzyl, p-methoxybenzyl, triphenylmethyl, or benzyloxymethyl; p-methoxyphenyl; and silyl groups such as trimethylsilyl. Preferred N-protecting groups include formyl, acetyl, benzoyl, pivaloyl, t-butylacetyl, phenylsulfonyl, benzyl, t-butyloxycarbonyl (Boc) and benzyloxycarbonyl (Cbz).

The compounds employed in the present invention can also be isotopically substituted. Preferred isotopic substitution include substitutions with stable or nonradioactive isotopes such as deuterium, $^{13}C$, $^{15}N$ or $^{18}O$. Incorporation of a heavy atom, such as substitution of deuterium for hydrogen, can give rise to an isotope effect that could alter the pharmacokinetics of the drug. In one example, at least 5 mol % (e.g., at least 10 mol %) of hydrogen in a compound used in the present invention is substituted with deuterium. In another example, at least 25 mole % of hydrogen in a compound used in the present invention is substituted with deuterium. In a further example, at least 50, 60, 70, 80 or 90 mole % of hydrogen in a compound employed in the present invention is substituted with deuterium. The natural abundance of deuterium is about 0.015%. Deuterium substitution or enrichment can be achieved, without limitation, by either exchanging protons with deuterium or by synthesizing the molecule with enriched or substituted starting materials. Other methods known in the art can also be used for isotopic substitutions.

It should be understood that the above-described embodiments and the following Scheme is given by way of illustration, not limitation. Various changes and modifications within the scope of the present invention will become apparent to those skilled in the art from the present description.
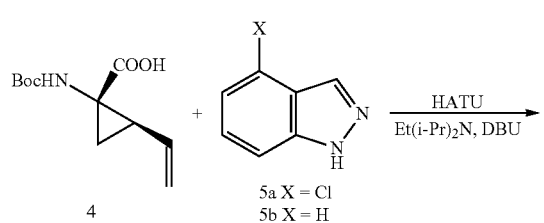
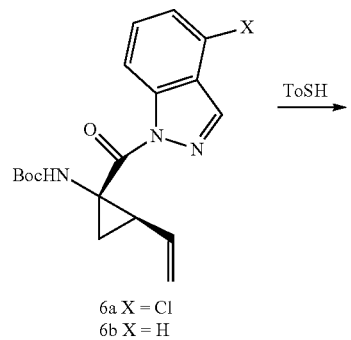
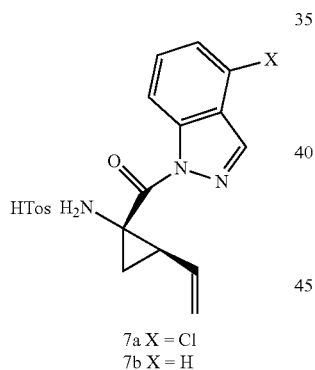
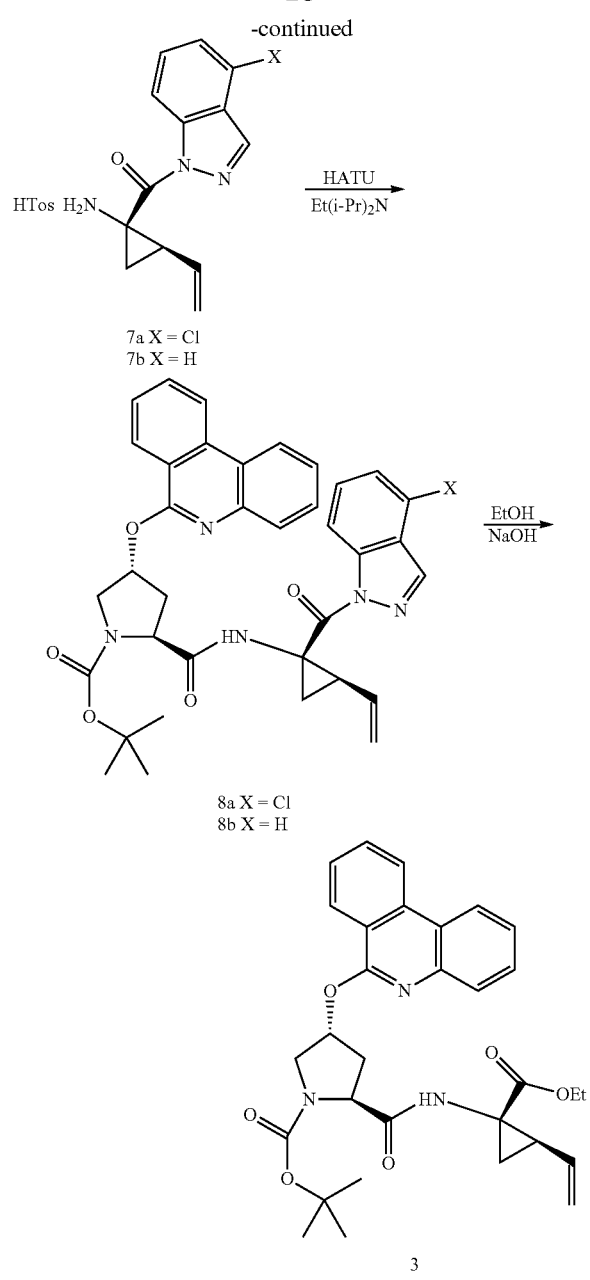
Step 1 Indazolide Preparation
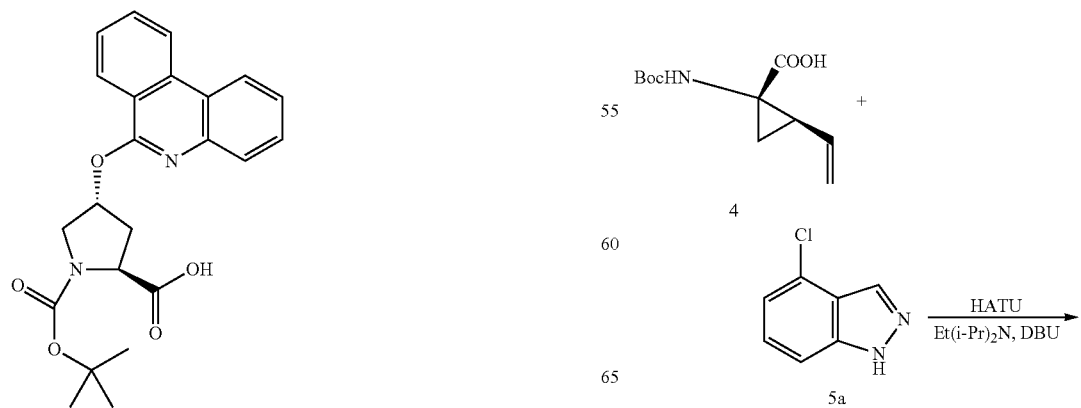

-continued

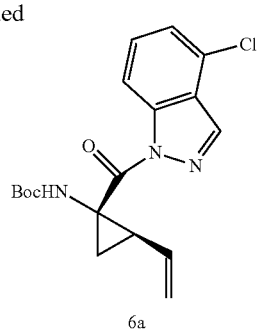

6a

Diisopropylethylamine (0.38 g, 3.0 mmol) was added to a solution of acid 4 (0.68 g, 3.0 mmol) and HATU (1.14 g, 3.0 mmol) in acetonitrile (7 mL). After mixing for 15 min at ambient temperature chloroindazole 5a (0.46 g, 3.0 mmol) and DBU (0.91 g, 6.0 mmol) were added to the reaction mixture. After additional 30 min at ambient temperature the mixture was diluted with ethyl acetate (15 mL) and transferred into 10% $KH_2PO_4$ (15 mL). The organic layer was separated and washed two times with 5% $KH_2PO_4$ (15 mL) and then with water (15 mL). The solution was concentrated to heavy oil (0.95 g, 93%).

As determined by $^1$H NMR the crude indazolide 6a contained small amounts of tetramethylurea and DBU salt side products. It was used in Step 2 without further purification.

$^1$H NMR (δ, DMSO-$d_6$): 1.15 (s, 9H), 1.26 (m, 1H), 1.92 (dd, 1H), 2.52 (dd, 1H), 4.95 (d, 1H), 5.16 (d, 1H), 5.38 (m, 1H), 7.48 (d, 1H), 7.61 (t, 1H), 7.8-7.9 (br. s, 1H), 8.17 (d, 1H), 8.54 (s, 1H)

Step 2 Deprotection

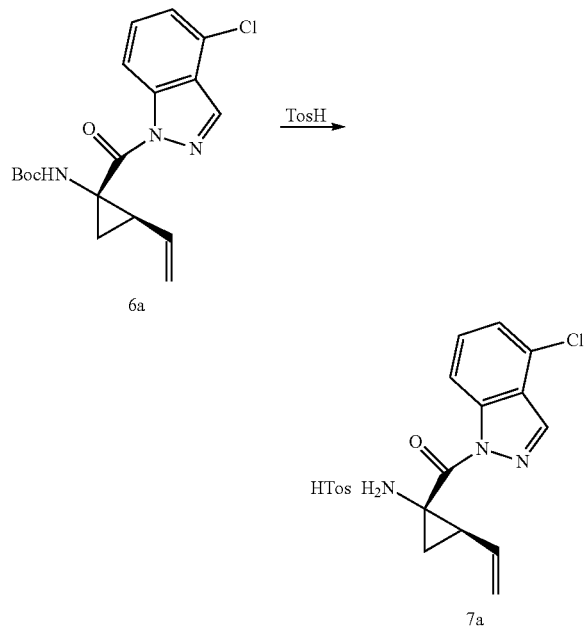

Indazolide 6a (0.31 g, 1.0 mmol) and toxic acid monohydrate (0.26 g, 1.5 mmol) were mixed in acetonitirle (5 mL) for 24 h at RT. The resulting precipitate was filtered off and dried to 0.3 g (80%) of tosylate salt 7a.

$^1$H NMR (δ, DMSO-$d_6$): 1.79 (m, 1H), 1.99 (dd, 1H), 2.28 (s, 3H), 2.60 (dd, 1H), 5.05 (d, 1H), 5.26 (d, 1H), 5.36 (m, 1H), 7.09 (d, 2H), 7.45 (d, 2H), 7.61 (d, 1H), 7.72 (t, 1H), 8.22 (d, 1H), 8.74 (s, 1H), 8.93 (br. s, 3H).

Step 3 Coupling

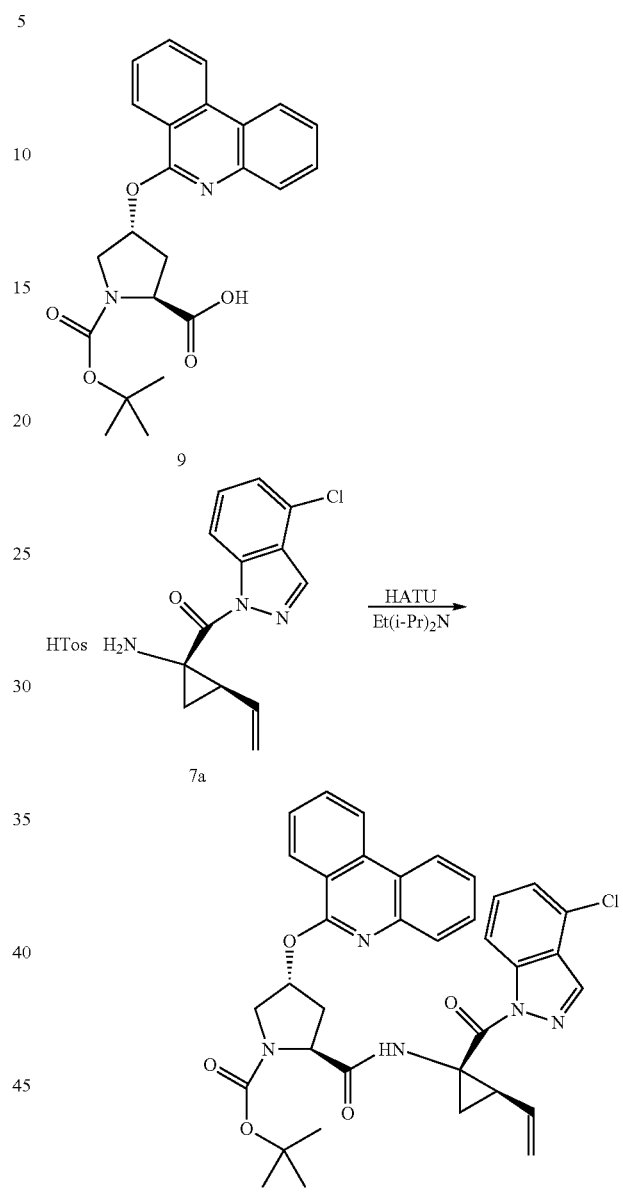

Diisopropylethylamine (0.09 g, 0.67 mmol) was added to a solution of prolinol derivative 9 (0.27 g, 0.67 mmol) and HATU (0.27 g, 0.7 mmol) in acetonitrile (7 mL). After mixing for 15 min at ambient temperature tosylate 7a (0.29 g, 0.67 mmol) and diisopropylethylamine (0.18 g, 1.34 mmol) were added to the reaction mixture. After additional 30 min at ambient temperature the precipitated product was filtered off and washed with acetonitrile-water (1:1, 5 mL). Drying under vacuum at 50° C. gave 0.4 g (92%) of indazolide 8a.

$^1$H NMR (δ, DMSO-$d_6$)*: 0.90, 1.06 (s, 9H), 1.29 (m, 1H), 1.99 (m, 1H), 2.18 (m, 1H), 2.51 (m, 1H), 3.54, 3,68 (d, 1H), 3.81 (m, 1H), 4.30 (t, 1H), 4.98 (m, 1H), 5.21 (m, 1H), 5.36 (m, 1H), 5.72, 5.78 (br. s, 1H), 7.39-7.58 (m, 2H), 7.58-7.70 (m, 2H), 7.75 (m, 1H), 7.93 (t, 1H), 8.08-8.26 (m, 2H), 8.46, 8.57 (s, 1H), 8.64 (d, 1H), 8.75 (d, 1H), 9.08, 9.12 (s, 1H).

*) ¹H NMR shows a mixture of 2 rotamers. When separated, the signals from the minor rotamer are shown in 'italics'

Step 4 Ethyl Ester Formation

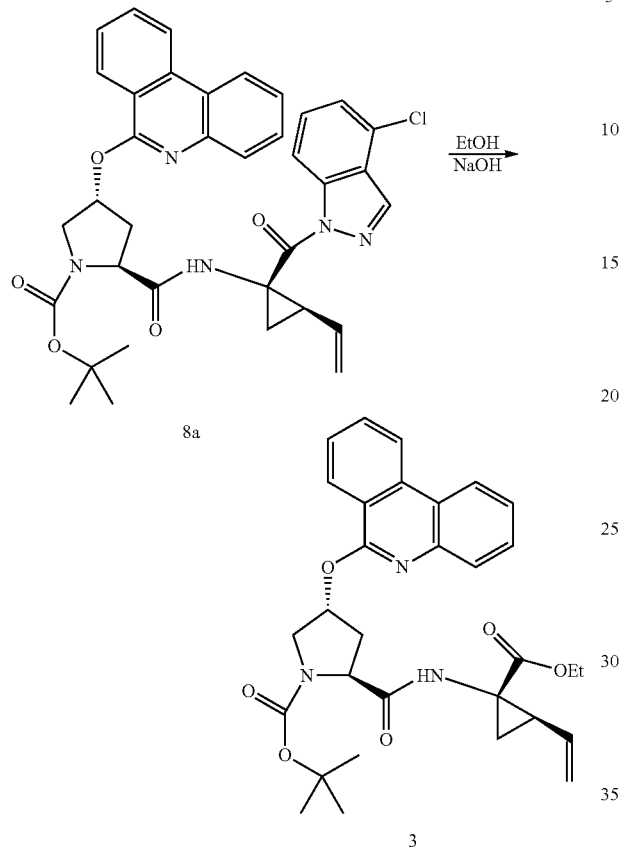

Sodium hydroxide (8.0 mg, 0.2 mmol) and indazolide 8a (0.13 g, 0.2 mmol) were mixed in ethanol (1.5 ml) for 15 min at ambient temperature. Water (1.5 mL) was added to the resulting clear solution to precipitate the product, which was filtered off and dried to give 0.089 g (82%) of ethyl ester 3.

¹H NMR (δ, DMSO-$d_6$): 1.17 (t, 3H), 1.30 (m, 1H), 1.35 (s, 9H), 1.66 (m, 1H), 2.18 (m, 1H), 2.37, (m, 1H), 2.60 (m, 1H), 3.6-3.8 (m, 1H), 3.92 (m, 1H), 4.06 (q, 2H), 4.32 (m, 1H), 5.11 (m, 1H), 5.25 (m, 1H), 5.66 (m, 1H), 5.82 (br. s, 1H), 7.54 (m, 1H), 7.65 (m, 1H), 7.73 (m, 1H), 7.80 (d, 1H), 7.93 (m, 1H), 8.24 (d, 1H), 8.64 (d, 1H), 8.74-8.76 (m, 2H).

tert-Butyl (1S,2R)-1-(1H-indazole-1-carbonyl)-2-vinylcyclopropylcarbamate (6b)

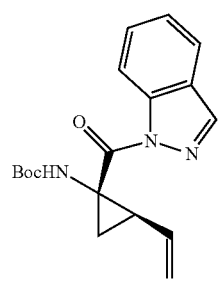

Crude indazolide 6b was prepared according Step 1 procedure in 95% yield.

¹H NMR (δ, DMSO-$d_6$): 1.15 (s, 9H), 1.26 (m, 1H), 1.92 (m, 1H), 2.52 (m, 1H), 4.95 (d, 1H), 5.16 (d, 1H), 5.38 (m, 1H), 7.39 (t, 1H), 7.60 (t, 1H), 7.66-7.80 (br. s, 1H) 7.85 (d, 1H), 8.21 (d, 1H), 8.46 (s, 1H)

(1S,2R)-1-Amino-2-vinylcyclopropyl)(1H-indazol-1-yl)methanone tosylate (7b

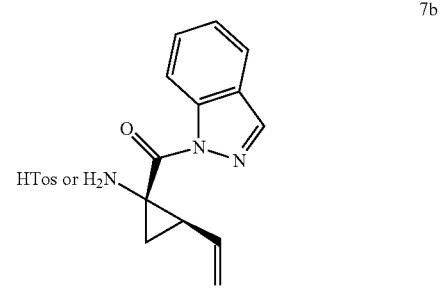

Indazolide 7b was prepared according Step 2 procedure in 66% yield. ¹H NMR (δ, DMSO-$d_6$): 1.77 (m, 1H), 1.97 (dd, 1H), 2.28 (s, 3H), 2.58 (dd, 1H), 5.04 (d, 1H), 5.26 (d, 1H), 5.36 (m, 1H), 7.09 (d, 2H), 7.45 (d, 2H), 7.51 (t, 1H), 7.71 (t, 1H), 7.97 (d, 1H), 8.26 (d, 1H), 8.69 (s, 1H), 8.92 (br. s, 3H).

(2S,4R)-tert-Butyl 2-((1S,2R)-1-(1H-indazole-1-carbonyl)-2-vinylcyclopropylcarbamoyl)-4-(phenanthridin-6-yloxy)pyrrolidine-1-carboxylate (8b)

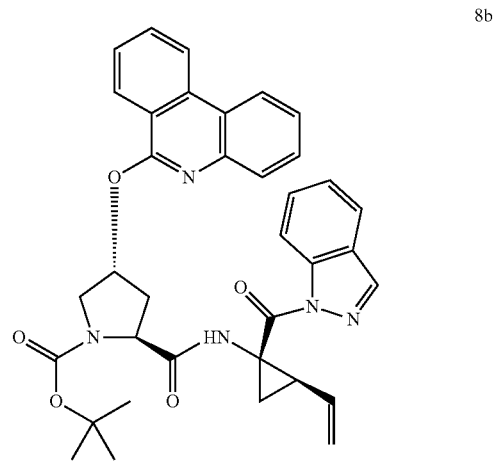 [SMILES: C=C[C@H]1C[C@@]1(NC(=O)[C@@H]1C[C@@H](Oc2nc3ccccc3c3ccccc23)CN1C(=O)OC(C)(C)C)C(=O)n1ncc2ccccc21]

Indazolide 8b was prepared according Step 3 procedure in 90% yield.

¹H NMR (δ, DMSO-$d_6$)*: 0.89, 1.14 (s, 9H), 1.30 (m, 1H), 1.96 (m, 1H), 2.17 (m, 1H), 2.51 (m, 1H), 3.68 (d, 1H), 3.83 (m, 1H), 4.31 (m, 1H), 4.95 (m, 1H), 5.20 (m, 1H), 5.35 (m, 1H), 5.72, 5.78 (br. s, 1H), 7.39 (m, 1H), 7.48-7.70 (m, 3H), 7.75 (m, 2H), 7.84 (d, 1H), 7.92 (t, 1H), 8.20 (m, 2H), 8.40, 8.49 (s, 1H), 8.63 (d, 1H), 8.75 (d, 1H), 8.99, (s, 1H).

*) ¹H NMR shows a mixture of 2 rotamers. When separated, the signals from the minor rotamer are shown in 'italics'

Indazolide 8b was converted into ester 3 according Step 4 procedure in 75% yield.

The foregoing description of the present invention provides illustration and description, but is not intended to be exhaustive or to limit the invention to the precise one disclosed. Modifications and variations are possible in light of the above teachings or may be acquired from practice of the invention. Thus, it is noted that the scope of the invention is defined by the claims and their equivalents.

What is claimed is:
1. A process, comprising:
reacting

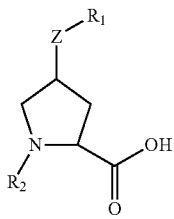

with

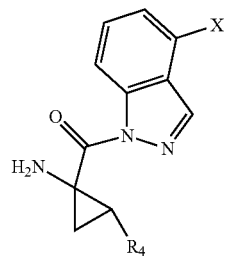

to form

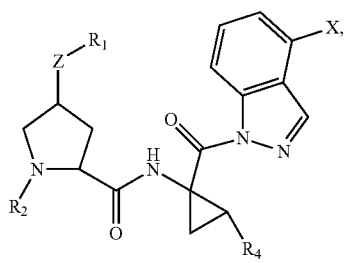

wherein:
Z is O, S, SO, $SO_2$, $N(R_N)$, OC(O), C(O)O, $N(R_N)C(O)$, or $C(O)N(R_N)$, wherein $R_N$ is H or optionally substituted $C_1$-$C_6$alkyl;
$R_1$ is optionally substituted $C_3$-$C_{10}$carbocycle or optionally substituted 5- to 10-membered heterocycle having at least one ring atom selected from nitrogen, oxygen, and sulfur;
$R_2$ is H or an amino protecting group selected from the group consisting of carboxybenzyl group, p-methoxybenzyl carbonyl group, tert-butyloxycarbonyl group, 9-fluorenylmethyloxycarbonyl group, acetyl group, benzoyl group, benzyl group, carbamate group, p-methoxybenzyl group, 3,4-dimethoxybenzyl group, p-methoxyphenyl group, tosyl group, and sulfonamide group;
$R_4$ is optionally substituted $C_1$-$C_6$alkyl, optionally substituted $C_2$-$C_6$alkenyl, or optionally substituted $C_2$-$C_6$alkynyl;
X is H or halogen; and
each optionally substituted $C_1$-$C_6$alkyl; $C_3$-$C_{10}$carbocycle, 5- to 10-membered heterocycle having at least one ring atom selected from nitrogen, oxygen, and sulfur, $C_2$-$C_6$alkenyl; or $C_2$-$C_6$alkynyl is optionally substituted with one or more substituents, each independently selected from the group consisting of —F, —Cl, —Br, —I, hydroxy, protected hydroxy, —$NO_2$, —$N_3$, —CN, —$NH_2$, protected amino, oxo, thioxo, —NH—$C_1$-$C_{12}$-alkyl, —NH—$C_2$-$C_8$-alkenyl, —NH—$C_2$-$C_8$-alkenyl, NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkenyl, —CONH—$C_3$-$C_{12}$-cycloalkyl, —CONH-aryl, CONH-heteroaryl, —CONH-heterocycloalkyl, —$OCO_2$—$C_1$-$C_{12}$-alkyl, —$OCO_2$—$C_2$-$C_8$-alkenyl, —$OCO_2$—$C_2$-$C_8$-alkenyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_8$-alkenyl, NHC(O)—$C_2$-$C_8$-alkenyl, —NHC(O)—$C_3$-$C_{12}$-cycloalkyl, —NHC(O)-aryl, NHC(O)-heteroaryl, —NHC(O)-heterocycloalkyl, —$NHCO_2$—$C_1$-$C_{12}$-alkyl, $NHCO_2$—$C_2$-$C_8$-alkenyl, —$NHCO_2$—$C_2$-$C_8$-alkynynl, —$NHCO_2$—$C_3$-$C_{12}$-cycloalkyl, —$NHCO_2$-aryl, —$NHCO_2$-heteroaryl, —$NHCO_2$-heterocycloalkyl, $NHC(O)NH_2$, —NHC(O)NH—$C_1$-$C_{12}$-alkyl, —NHC(O)NH—$C_2$-$C_8$-alkenyl, NHC(O)NH—$C_2$-$C_8$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, $NHC(S)NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —$NHC(NH)NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, NHC(NH)NH—$C_3$-$C_{12}$-cycloalkyl, —NHC(NH)NH-aryl, —NHC(NH)NH— heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)— heterocycloalkyl, —C(NH)NH—$C_1$-$C_{12}$-alkyl, —C(NH)NH—$C_2$-$C_8$-alkenyl, C(NH)NH—$C_2$-$C_8$-alkynyl, —C(NH)NH—$C_3$-$C_{12}$-cycloalkyl, —C(NH)NH-aryl, C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —$SO_2NH_2$, —$SO_2$NH—$C_1$-$C_{12}$-alkyl, —$SO_2$NH—$C_2$-$C_8$-alkenyl, —$SO_2$NH—$C_2$-$C_8$-alkynyl, —$SO_2$NH—$C_3$-$C_{12}$-cycloalkyl, —$SO_2$NH-aryl, —$SO_2$NH-heteroaryl, —$SO_2$NH-heterocycloalkyl, NHSO₂—C₁-C₁₂-alkyl, —NHSO₂—C₂-C₈-alkenyl, —NHSO₂—C₂-C₈-alkynyl, —NHSO₂—C₃-C₁₂-cycloalkyl, —NHSO₂-aryl, —NHSO₂-heteroaryl, —NHSO₂-heterocycloalkyl, —CH₂NH₂, —CH₂SO₂CH₃, -aryl, -arylalkyl, -heteroaryl, -heteroarylalkyl, -heterocycloalkyl, —C₃-C₁₂-cycloalkyl, polyalkoxyalkyl, polyalkoxy, -methoxymethoxy, -methoxyethoxy, —SH, —S—C₁-C₁₂-alkyl, —S—C₂-C₈-alkenyl, —S—C₂-C₈-alkynyl, —S—C₃-C₁₂-cycloalkyl, —S-aryl, -heteroaryl, —S-heterocycloalkyl, and methylthiomethyl.

2. A process comprising:
reacting

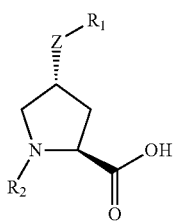

with

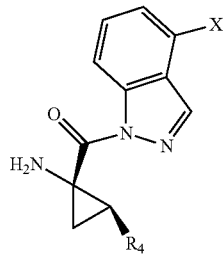

to form

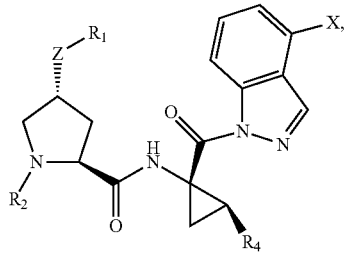

wherein:
Z is O, S, SO, SO₂, N(R_N), OC(O), C(O)O, N(R_N)C(O), or C(O)N(R_N), wherein R_N is H or optionally substituted C₁-C₆alkyl;

R₁ is optionally substituted C₃-C₁₀carbocycle or optionally substituted 5- to 10-membered heterocycle having at least one ring atom selected from nitrogen, oxygen, and sulfur;

R₂ is H or an amino protecting group selected from the group consisting of carboxybenzyl group, p-methoxybenzyl carbonyl group, tert-butyloxycarbonyl group, 9-fluorenylmethyloxycarbonyl group, acetyl group, benzoyl group, benzyl group, carbamate group, p-methoxybenzyl group, 3,4-dimethoxybenzyl group, p-methoxyphenyl group, tosyl group, and sulfonamide group;

R₄ is optionally substituted C₁-C₆alkyl, optionally substituted C₂-C₆alkenyl, or optionally substituted C₂-C₆alkynyl;

X is H or halogen; and each optionally substituted C₁-C₆alkyl; C₃-C₁₀carbocycle, 5- to 10-membered heterocycle having at least one ring atom selected from nitrogen, oxygen, and sulfur, C₂-C₆alkenyl; or C₂-C₆alkynyl is optionally substituted with one or more substituents, each independently selected from the group consisting of —F, —Cl, —Br, —I, hydroxy, protected hydroxy, —NO₂, —N₃, —CN, —NH₂, protected amino, oxo, thioxo, —NH—C₁-C₁₂-alkyl, —NH—C₂-C₈-alkenyl, —NH—C₂-C₈-alkenyl, NH—C₃-C₁₂-cycloalkyl, —NH-aryl, —NH-heteroaryl, —NH-heterocycloalkyl, -dialkylamino, -diarylamino, -diheteroarylamino, —O—C₁-C₁₂-alkyl, —O—C₂-C₈-alkenyl, —O—C₂-C₈-alkenyl, —O—C₃-C₁₂-cycloalkyl, —O-aryl, —O-heteroaryl, —O-heterocycloalkyl, —C(O)—C₁-C₁₂-alkyl, —C(O)—C₂-C₈-alkenyl, —C(O)—C₂-C₈-alkynyl, —C(O)—C₃-C₁₂-cycloalkyl, —C(O)-aryl, —C(O)-heteroaryl, C(O)-heterocycloalkyl, —CONH₂, —CONH—C₁-C₁₂-alkyl, —CONH—C₂-C₈-alkenyl, —CONH—C₂-C₈-alkenyl, —CONH—C₃-C₁₂-cycloalkyl, —CONH-aryl, —CONH-heteroaryl, —CONH-heterocycloalkyl, —OCO₂—C₁-C₁₂-alkyl, —OCO₂—C₂-C₈-alkenyl, —OCO₂—C₂-C₈-alkenyl, —OCO₂—C₃-C₁₂-cycloalkyl, —OCO₂-aryl, —OCO₂-heteroaryl, —OCO₂-heterocycloalkyl, —OCONH₂, —OCONH—C₁-C₁₂-alkyl, —OCONH—C₂-C₈-alkenyl, —OCONH—C₂-C₈-alkynyl, —OCONH—C₃-C₁₂-cycloalkyl, —OCONH-aryl, —OCONH-heteroaryl, —OCONH-heterocycloalkyl, —NHC(O)—C₁-C₁₂-alkyl, —NHC(O)—C₂-C₈-alkenyl, NHC(O)—C₂-C₈-alkenyl, —NHC(O)—C₃-C₁₂-cycloalkyl, —NHC(O)-aryl, NHC(O)-heteroaryl, —NHC(O)-heterocycloalkyl, —NHCO₂—C₁-C₁₂-alkyl, NHCO₂—C₂-C₈-alkenyl, —NHCO₂—C₂-C₈-alkynynl, —NHCO₂—C₃-C₁₂-cycloalkyl, —NHCO₂-aryl, —NHCO₂-heteroaryl, —NHCO₂-heterocycloalkyl, NHC(O)NH₂, —NHC(O)NH—C₁-C₁₂-alkyl, —NHC(O)NH—C₂-C₈-alkenyl, NHC(O)NH—C₂-C₈-alkenyl, —NHC(O)NH—C₃-C₁₂-cycloalkyl, —NHC(O)NH-aryl, —NHC(O)NH-heteroaryl, —NHC(O)NH-heterocycloalkyl, NHC(S)NH₂, —NHC(S)NH—C₁-C₁₂-alkyl, —NHC(S)NH—C₂-C₈-alkenyl, —NHC(S)NH—C₂-C₈-alkynyl, —NHC(S)NH—C₃-C₁₂-cycloalkyl, —NHC(S)NH-aryl, —NHC(S)NH-heteroaryl, —NHC(S)NH-heterocycloalkyl, —NHC(NH)NH₂, —NHC(NH)NH—C₁-C₁₂-alkyl, —NHC(NH)NH—C₂-C₈-alkenyl, —NHC(NH)NH—C₂-C₈-alkynyl, —NHC(NH)NH—C₃-C₁₂-cycloalkyl, —NHC(NH)NH-aryl, —NHC(NH)NH-heteroaryl, —NHC(NH)NH-heterocycloalkyl, —NHC(NH)—C₁-C₁₂-alkyl, —NHC(NH)—C₂-C₈-alkenyl, —NHC(NH)—C₂-C₈-alkynyl, —NHC(NH)—C₃-C₁₂-cycloalkyl, —NHC(NH)-aryl, —NHC(NH)-heteroaryl, —NHC(NH)— heterocycloalkyl, —C(NH)NH—C₁-C₁₂-alkyl, —C(NH)NH—C₂-C₈-alkenyl, C(NH)NH—C₂-C₈-alkynyl, —C(NH)NH—C₃-C₁₂-cycloalkyl, —C(NH)NH-aryl, C(NH)NH-heteroaryl, —C(NH)NH-heterocycloalkyl, —S(O)—C₁-C₁₂-alkyl, —S(O)—C₂-C₈-alkenyl, —S(O)—C₂-C₈-alkynyl, —S(O)—C₃-C₁₂-cycloalkyl, —S(O)-aryl, —S(O)-heteroaryl, —S(O)-heterocycloalkyl, —SO₂NH₂, —SO₂NH—C₁-C₁₂-alkyl, —SO₂NH—C₂-C₈-alkenyl, —SO₂NH—C₂-C₈-alkynyl, —SO₂NH—C₃-C₁₂-cycloalkyl, —SO₂NH-aryl, —SO₂NH-heteroaryl, —SO$_2$NH-heterocycloalkyl, NHSO$_2$—C$_1$-C$_{12}$-alkyl, —NHSO$_2$—C$_2$-C$_8$-alkenyl, —NHSO$_2$—C$_2$-C$_8$-alkynyl, NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_8$-alkenyl, —S—C$_2$-C$_8$-alkynyl, —S—C$_3$-C$_{12}$-cycloalkyl, —S-aryl, -heteroaryl, —S-heterocycloalkyl, and methylthiomethyl.

3. The process of claim 2, further comprising reacting

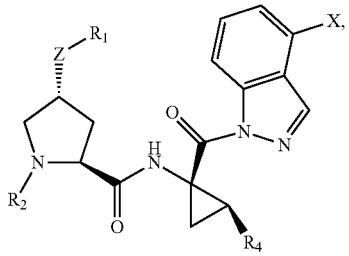

with R$_3$—OH to form

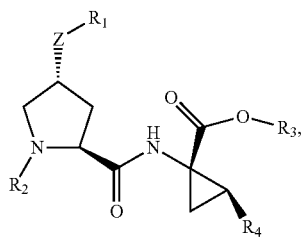

wherein R$_3$ is optionally substituted C$_1$-C$_6$alkyl.

4. The process according to claim 3, wherein:
Z is O;
R$_1$ is phenanthridine;
R$_2$ is tert-butyloxycarbonyl;
R$_4$ is vinyl;
X is H or Cl; and
R$_3$ is —CH$_2$CH$_3$.

5. A process comprising:
coupling

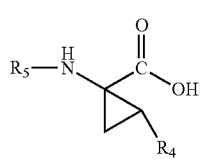

with

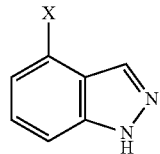

to form

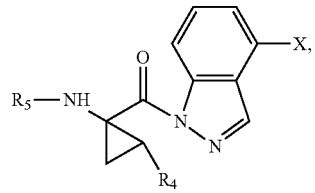

wherein:
R$_4$ is optionally substituted C$_1$-C$_6$alkyl, optionally substituted C$_2$-C$_6$alkenyl, or optionally substituted C$_2$-C$_6$alkynyl;
X is H or halogen;
R$_5$ is H or an amino protecting group selected from the group consisting of carboxybenzyl group, p-methoxybenzyl carbonyl group, tert-butyloxycarbonyl group, 9-fluorenylmethyloxycarbonyl group, acetyl group, benzoyl group, benzyl group, carbamate group, p-methoxybenzyl group, 3,4-dimethoxybenzyl group, p-methoxyphenyl group, tosyl group, and sulfonamide group; and
each optionally substituted C$_1$-C$_6$alkyl, C$_2$-C$_6$alkenyl, or C$_2$-C$_6$alkynyl is optionally substituted with one or more substituents, each independently selected from the group consisting of —F, —Cl, —Br, —I, hydroxy, protected hydroxy, —NO$_2$, —N$_3$, —CN, —NH$_2$, protected amino, oxo, thioxo, —NH—C$_1$-C$_{12}$-alkyl, —NH—C$_2$-C$_8$-alkenyl, —NH—C$_2$-C$_8$-alkynyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_8$-alkenyl, —O—C$_2$-C$_8$-alkenyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_8$-alkenyl, —C(O)—C$_2$-C$_8$-alkenyl, —C(O)—C$_3$-C$_{12}$-cycloalkyl, C(O)-aryl, —C(O)-heteroaryl, —C(O)-heterocycloalkyl, —CONH$_2$, —CONH—C$_1$-C$_{12}$-alkyl, —CONH—C$_2$-C$_8$-alkenyl, —CONH—C$_2$-C$_8$-alkenyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_8$-alkenyl, —OCO$_2$—C$_2$-C$_8$-alkynyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_8$-alkenyl, —OCONH—C$_2$-C$_8$-alkenyl, —OCONH—C$_3$-C$_{12}$-cycloalkyl, —OCONH-aryl, —OCONH-heteroaryl, —OCONH-heterocycloalkyl, —NHC(O)—C$_1$-C$_{12}$-alkyl, —NHC(O)—C$_2$-C$_8$-alkenyl, —NHC(O)—C$_2$-C$_8$-alkynyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_8$-alkenyl, —NHCO$_2$—C$_2$-C$_8$-alkynynl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, —NHC(O)NH—C$_1$-C$_{12}$-alkyl, —NHC(O)NH—C$_2$-C$_8$-alkenyl, —NHC(O)NH—C$_2$-C$_8$-alkynyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, —NHC(S)NH—C$_1$-C$_{12}$-alkyl, —NHC(S)NH—C$_2$-C$_8$-alkenyl, —NHC(S)NH—C$_2$-C$_8$-alkynyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_8$-alkenyl, —NHC(NH)NH—C$_2$-C$_8$-alkynyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_8$-alkenyl, —NHC(NH)—C$_2$-C$_8$-alkynyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —(NH)NH—C$_2$-C$_8$-alkenyl, —C(NH)NH—C$_2$-C$_8$-alkynyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_8$-alkenyl, —S(O)—C$_2$-C$_8$-alkynyl, —S(O)—C$_3$-C$_{12}$-cycloalkyl, —S(O)-aryl, —S(O)-heteroaryl, —S(O)-heterocycloalkyl, —SO$_2$NH$_2$, —SO$_2$NH—C$_1$-C$_{12}$-alkyl, —SO$_2$NH—C$_2$-C$_8$-alkenyl, —SO$_2$NH—C$_2$-C$_8$-alkynyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_8$-alkenyl, —NHSO$_2$—C$_2$-C$_8$-alkynyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_8$-alkenyl, —S—C$_2$-C$_8$-alkynyl, —S—C$_3$-C$_{12}$-cycloalkyl, —S-aryl, -heteroaryl, —S-heterocycloalkyl, and methylthiomethyl.

6. The process according to claim 2, wherein:
Z is O;
R$_1$ is phenanthridine;
R$_2$ is tert-butyloxycarbonyl;
R$_4$ is vinyl; and
X is H or Cl.

\* \* \* \* \*